United States Patent [19]

Croset et al.

[11] Patent Number: 5,106,480
[45] Date of Patent: Apr. 21, 1992

[54] DEVICE OF THE SOLID-ELECTROLYTE ELECTROCHEMICAL CELL TYPE

[75] Inventors: Michel Croset; Gonzalo Velasco; Philippe Schnell, all of Paris, France

[73] Assignee: Thomson-CSF, Paris, France

[21] Appl. No.: 653,997

[22] Filed: Feb. 13, 1991

Related U.S. Application Data

[63] Continuation of Ser. No. 407,054, Sep. 14, 1989, abandoned, which is a continuation of Ser. No. 143,264, Jan. 1, 1988, abandoned, which is a continuation of Ser. No. 821,210, Jan. 23, 1986, abandoned, which is a continuation of Ser. No. 649,790, Sep. 12, 1984, abandoned, which is a continuation of Ser. No. 297,080, Aug. 27, 1981, abandoned.

[51] Int. Cl.⁵ .................................... G01N 27/406
[52] U.S. Cl. .................................... 204/424; 204/421; 204/426
[58] Field of Search ............... 204/153.18, 421–429

[56] References Cited

U.S. PATENT DOCUMENTS

| 3,607,424 | 9/1971 | Maki et al. | 204/427 |
| 3,776,831 | 12/1973 | Roy et al. | 204/422 |
| 4,121,988 | 10/1978 | Sano et al. | 204/428 |
| 4,152,234 | 5/1979 | Pollner | 204/427 |
| 4,208,265 | 6/1980 | Hori et al. | 204/424 |
| 4,210,509 | 7/1980 | Obayashi et al. | 204/427 |
| 4,272,350 | 6/1981 | Croset et al. | 204/426 |
| 4,354,912 | 10/1982 | Friese | 204/429 |

FOREIGN PATENT DOCUMENTS 2650850 11/1978 Fed. Rep. of Germany ...... 204/421

Primary Examiner—T. Tung
Attorney, Agent, or Firm—Oblon, Spivak, McClelland, Maier & Neustadt

[57] ABSTRACT

A device comprising an inhomogeneous solid electrolyte of doped materials which are exclusive conductors for a predetermined chemical species. The electrolyte has a first region and a second surface region, the thickness of which is usually less than 400 Å. In a first alternative embodiment, the second region is formed by increasing the doping percentage of the material constituting the first region. In a second alternative embodiment, the second region is formed by depositing a thin film of doped material chosen so as to ensure that the work function to be provided by the predetermined chemical species is of lower value than in the case of the doped material constituting the first region.

2 Claims, 3 Drawing Sheets

DEVICE OF THE SOLID-ELECTROLYTE ELECTROCHEMICAL CELL TYPE

This is a continuation of application Ser. No. 407,054, filed on Sept. 14, 1989, now abandoned which is a continuation of Ser. No. 143,264, filed on Jan. 1, 1988, which is a continuation of Ser. No. 821,210, filed on Jan. 23, 1986, which is a continuation of Ser. No. 649,790 filed on Sept. 12, 1984, which is a continuation of Ser. No. 297,080, filed on Aug. 27, 1981, all now abandoned.

This invention relates to a device of the solid-electrolyte electrochemical-cell type and to a method for the fabrication of said device. The invention is directed in particular to an electrochemical sensor for measuring the concentration of species in a fluid mixture.

One of the well-known families of sensors for determining the composition of chemical species or measuring, for example, partial pressures of species which are present in a gas in fact makes use of an electrochemical cell of the concentration type. A cell of this type comprises a first electrode or so-called measuring electrode, a solid electrolyte and a second so-called reference electrode which is in contact with a reference medium. The measuring electrode is contacted with the medium to be analyzed such as the exhaust gases of an internal combustion engine, for example. These gases contain in particular oxygen, carbon monoxide, carbon dioxide and different hydrocarbons. The electrolyte is a selective ionic conductor for the species to be analyzed.

In a first design approach of prior art sensors, the reference medium is ambient air or at least a reservoir containing a suitable gas. The most common form of a sensor of this type is known as a "glove finger". The central portion is constituted by a solid electrolyte, the inner or outer faces of which are covered by electrodes. The interior of the "finger" usually communicates with the atmosphere and the exterior of said finger communicates with the medium to be analyzed. Since the electrolyte usually has to serve as a mechanical support for the complete assembly, provision is thus made for an electrode of substantial thickness.

Sensors of this type are commonly employed in the field of automobile electronics for measuring the partial pressure of oxygen in exhaust gases. One example of a sensor of this type is described in French patent No. 2,224,043.

A second approach of the prior art proposes the use of a means for combining the electrode function and the reference medium function. To this end, there is employed an electrode based on a combination of the type: "M—MX", where M is a metal and X is oxygen or a halogen to be detected such as "M—MO", for example, in the case of detection of oxygen. So far as sensors for measuring the partial pressure of oxygen are concerned, it is well-known that the following equations govern these sensors:

at the interfaces between electrodes and electrolytes:

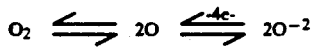

the potential difference $\Delta V$ in volts which is accordingly developed between the electrodes is given by the Nernst law:

$$\Delta V = \frac{RT}{4F} \ln \frac{P_1}{P_2}$$

with $R$ = gas constant (ideal gases) = 8.314 J(mole.K)
$F$ = Fraraday number = 96490 C.mole$^{-1}$
$T$ = absolute temperature in degrees Kelvin
$P_1$ and $P_2$ = partial pressures in the media which are in contact with the two electrodes.

In the most common applications of these sensors including measurement of the partial pressure of oxygen in exhaust gases, the operating temperatures are usually above 450° C. In this case the rise time of the electromotive force measured between the electrodes in response to a variation in partial pressure of the species to be measured such as oxygen, for example, is typically less than one second. Below this temperature, the response time increases appreciably, thus limiting the use of a cell of this type to the measurement of slow and even very slow phenomena. This deterioration of dynamic performances of the cell may be attributed to a number of causes: to the electrode reaction resistances and capacitances, to the resistance, to the ionic conduction of the electrolyte and to the capacitances of the electric measuring circuit which is associated with the cell. In fact, since the equivalent impedance of a cell of this type is of very high value, the capacitances of the connecting cables or of the instrument which measures the interelectrode electromotive force play a part in the deterioration of the response time. Typical values of these capacitances are of the order of 5 to 20 pF.

Experience has shown that the first cause or in other words the time constant of the electrode reactions becomes predominant in the lengthening of the response time when the operating temperature falls below a value of about 250° C.

In order to achieve an improvement in the two above-mentioned sensor design approaches, it has also been proposed to adopt thin-film deposition techniques, especially with a view to optimizing the resistance of the electrolyte to ionic conduction.

If measurement of the partial pressure of oxygen in a gas is again taken as an example in regard to electrode reactions, a number of different stages may be distinguished:

1) absorption of molecular oxygen at the surface of the measuring electrode;
2) dissociation of said molecular oxygen into two oxygen atoms;
3) diffusion towards the points of exchange with the electrolyte;
4) the exchange process proper.

By way of example, these phenomena are described in the article by Schouler et alia, entitled "Application according to Bauerle of the curve tracing of complex admittance diagrams in electrochemistry of solids" which appeared in the French review "Journal de Chimie Physique", 1973, vol. 70, No 6, pages 923–935. It may reasonably be concluded from practical experience that the exchange process is the main underlying cause of limitation of the dynamic performances of the cell. A reduction of the response time is thus conditioned by the increase in exchange currents at the electrode-electrolyte interface.

The invention proposes to meet this requirement.

It is therefore an aim of the invention to provide a device of the electrochemical cell type comprising a solid electrolyte having the structure of a crystal lattice consisting of material which is doped in such a manner as to create vacancies in the lattice. Said electrolyte is an ionic conductor for a predetermined chemical species and is in contact with two conducting electrodes. The device is mainly distinguished by the fact that a first region of the electrolyte has a first doping percentage and that a second surface region has a second doping percentage, said second region being adapted to cover at least that surface of the first region which is subjacent to at least one of the electrodes and the second percentage being chosen so as to be higher than the first in order to increase the number of vacancies created in the lattice.

The invention is also concerned with a method for the fabrication of a device of this type.

Other features of the invention will be more apparent upon consideration of the following description and accompanying drawings, wherein.

By way of illustration, the invention will hereinafter be described with more specific reference to the measurement of relative concentrations of reactive species in a fluid mixture without thereby implying any limitation in the scope of the present invention.

In more precise terms, if the application under consideration consists in detecting oxygen in the exhaust gases of an internal combustion engine, a typical example of oxygen-conducting solid electrolyte in ionic form is calcium-stabilized zirconium corresponding to the formula:

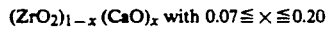

$(ZrO_2)_{1-x}(CaO)_x$ with $0.07 \leq x \leq 0.20$

The values of x given above are usually accepted by different authors of scientific articles in this field and correspond to a cubic crystal phase of zirconia. The crystal lattice structure has $O^-$ oxygen ion acceptor vacancies. Zirconia which has thus been doped is consequently an ionic conductor of oxygen. The ionic conductivity increases with the concentration of dopants to $(ZrO_2)_{0.85}(CaO)_{0.15}$ but decreases beyond this composition, this decrease being brought about by mechanisms which are not well known. A corresponding doping to the value $x=0.15$ therefore permits optimization of ionic conduction. However, as already recalled, the response time is slowed-down by the difficulty of ionic exchanges at the interface between solid electrolyte and external medium.

In the case under consideration, said external medium can be constituted by a platinum electrode within which molecular oxygen is dissociated so as to produce oxygen ions. When a sensor of this type is employed at high temperatures ($>400°$ C.), the response time is less than one second and therefore of sufficiently short duration for the majority of applications. Should it be desired to employ sensors of this type at lower temperatures, said response time increases to an appreciable extent and limits the application of these sensors to slow or very slow phenomena.

Figure 1:
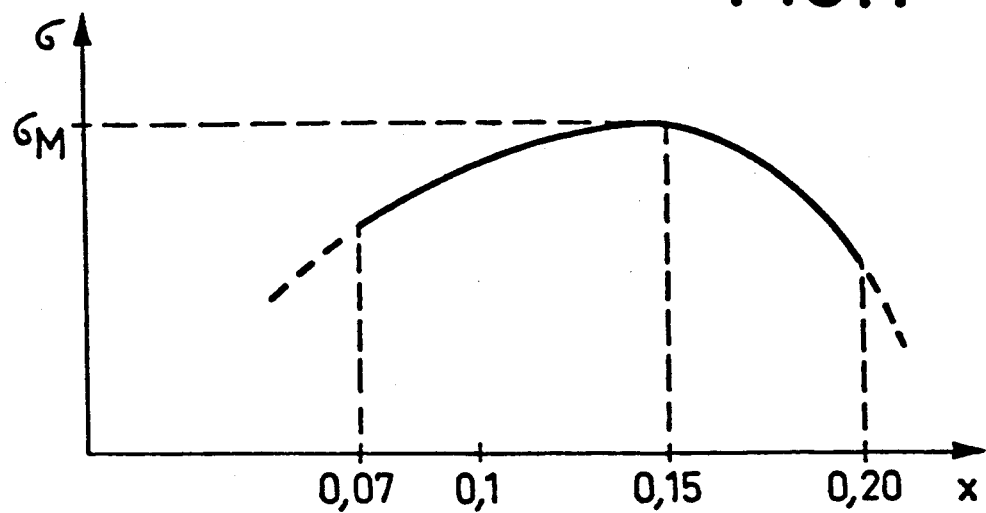
FIGS. 1 to 4 are explanatory diagrams of the phenomena involved in the invention.

FIG. 1 illustrates the variation of ionic conductivity $\sigma$ as a function of x; this conductivity passes through a maximum $\sigma_M$ in respect of the value $x=0.15$. The book by J. Hladik, entitled "Physics of Electrolytes", volume 2: "Thermodynamics and Electrode Processes in Solid State Electrolytes" and published in London by the Academic Press is primarily devoted to a study of these phenomena.

Although the value $x=0.15$ is usually adopted and permits optimization of ionic conduction, this value is not optimum, however, in the case of exchanges occurring at the interface between solid electrolyte and external medium. These exchanges would be facilitated by a higher density of oxygen vacancies and therefore a higher concentration of calcium oxide.

In order to achieve simultaneous optimization of these two parameters, the invention proposes the use of solid electrolytes having at least two regions:

a first region constituting the greater part of the electrolyte and doped so as to optimize the ionic conduction, this doping being designated hereinafter as normal doping $D_N$;

and a second surface region of small thickness which is overdoped and intended to promote ionic exchanges at the interface. Ideally, said second region should have a thickness corresponding to a few atomic layers. Maximum doping is $D_M$.

Figure 2:
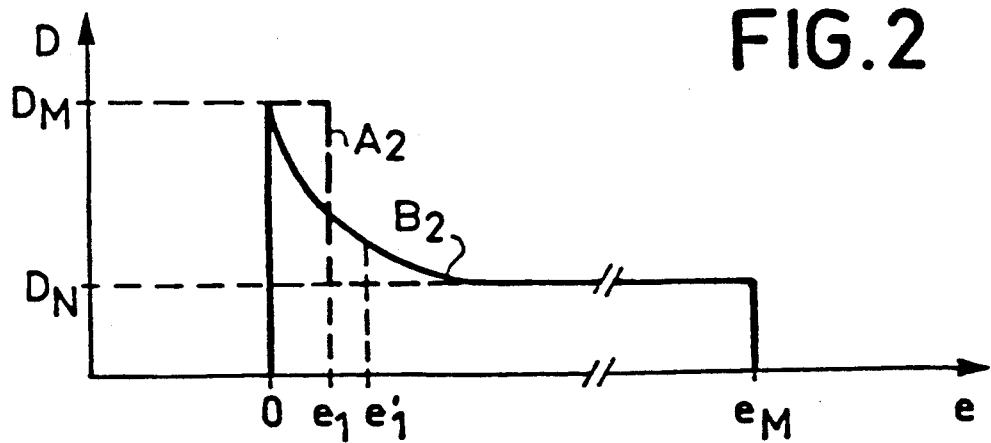

By means of the curve $A_2$, FIG. 2 illustrates the ideal variation in doping as a function of the thickness e of the electrolyte. The electrolyte thickness varies between the values O and $e_M$ whilst the surface region varies between the values O and $e_1$. In actual practice, the methods which can be employed for obtaining this overdoping do not make it possible to obtain this ideal curve. All the methods of fabrication usually employed in the field of microelectronics may be adopted within the framework of the present invention including, for example, the methods of ion implantation or diffusion.

The curve $B_2$ represents a typical profile of the surface variation of doping of the electrolyte. It follows from this curve that the overdoped region has a thickness equivalent to $e'_1$ which is greater than the theoretical value $e_1$.

Should it be desired to come close to ideal conditions, a number of methods may be adopted. After the stage consisting of overdoping of the surface region of the electrolyte to a depth $e'_1$, the electrolyte is eroded by chemical attack, for example, in order to remove a layer $\Delta e$ of material. In consequence, the overdoped region has only a thickness equal to $e_0 - e'_1$. Maximum doping decreases from the value $D_{M1}$ to the slightly lower value $D_{M2}$.

Figure 4:
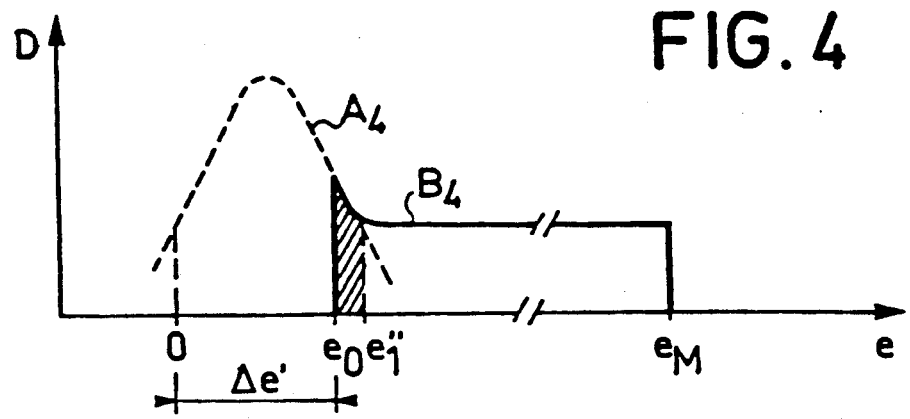

Another method consists in covering the electrolyte with a layer of another material which can be more readily attacked than the material constituting the electrolyte. In the case of zirconium, this material can consist of a thin film of metal such as silver or of an oxide such as niobium oxide ($Nb_2O_5$) or silicon oxide ($SiO_2$). These oxides can be attacked with hydrofluoric acid. In this case, overdoping will be carried out by ion implantation. In FIG. 4, the curve $A_4$ represents the profile of variation in doping in the form of a Gauss curve obtained by ion implantation. The thickness of the layer of material deposited on the electrolyte is equal to $\Delta e'$. Overdoping extends within the electrolyte itself to a depth which is substantially equal to $e_0 - e''_1$. When the doping operation has been completed, the surface layer of material is removed by chemical attack and the overdoped region is reduced to a region of the electrolyte having a depth $e_0'0 - e''_1$. The energy imparted to the calcium ions depends on the thickness of the deposited layer $\Delta e'$ which may vary between a few hundreds of angströms to a few thousand angströms. The corresponding energies will vary typically within the range of 10 to 400 KeV. Another means of reducing the thickness of the overdoped layer consists of ionic erosion, plasma attack after implantation or else erosion at the same time as implantation performed at low energy ($< 30$ keV).

Finally, overdoping may also be obtained by deposition of a surface layer of heavily doped zirconia by vacuum evaporation, cathodic sputtering or any other suitable methods.

The thickness of the deposit may be of the order of 50 Å. In this case, the deposited material and the dopant may be different from those of the first region of the electrolyte.

Figure 5:
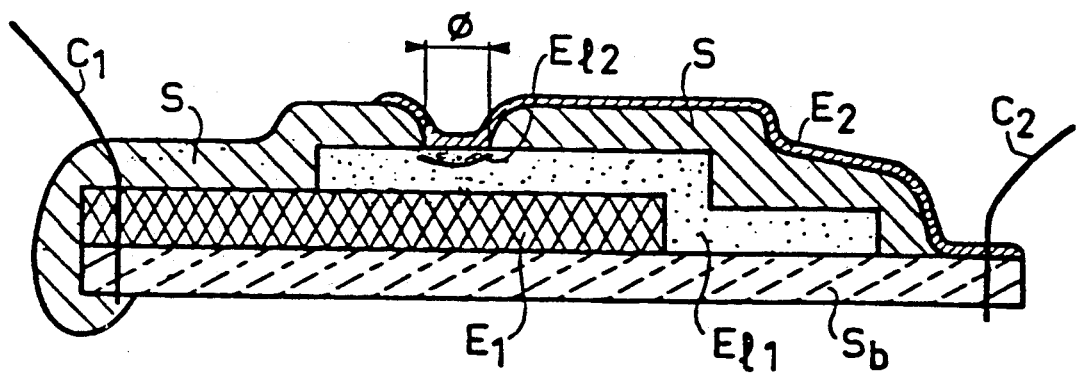
FIG. 5 shows one example of an electrochemical sensor fabricated in accordance with a first alternative embodiment of the invention.

In order to illustrate the invention, an electrochemical sensor for measuring relative concentrations of oxygen in a gas will now be described with reference to FIG. 5. When fabricated in accordance with the present invention, said sensor has a general structure of the type described in particular in European patent Application published under No 12 647. A reference electrode $E_1$ and a zirconia strip have been deposited by cathodic sputtering on an insulating substrate $S_b$ of monocrystalline alumina, for example, which endows the complete assembly with the necessary mechanical strength. Said reference electrode is of the "nickel-nickel oxide" type and is designed in the form of a small tongue having a thickness of 1 $\mu$m. Said zirconia strip consists of stabilized zirconia having the composition $(ZrO_2)_{0.85} (CaO)_{0.15}$, has a thickness of 1 $\mu$m and partially overlaps the reference electrode $E_1$. Electrical contact with the "nickel-nickel oxide" electrode is established by means of a platinum wire $C_1$. In order to prevent oxidation of the nickel by contact with the external medium in which the gases to be analyzed are flowing, a coating S of enamel protects the entire structure except for a circular zone $\phi$ having a surface area of approximately 0.1 mm$^2$. As a result of ion implantation, a dose of approximately $2.6 \times 10^{16}$ calcium atoms per cm$^2$ has been implanted into the electrolyte $E_{l1}$ at an energy of 30 KeV so as to form a surface region $E_{l2}$ of overdoped electrolyte. Ion implantation is followed by a heat treatment in air at 800° C. for a period of 10 minutes. After this treatment, there is formed an overdoped region of the electrolyte having the approximate composition $(ZrO_2)_{0.70} (CaO)_{0.30}$ to a depth of about 300 Å.

A thin layer of platinum lacquer is deposited on the zirconia surface which has remained free and also on a portion of the enamel S so as to constitute the measuring electrode $E_2$. A second platinum wire constitutes a second electrical contact $C_2$. The interelectrode potential is collected between these two conductors and the signals thus collected are transmitted to electronic circuits which are not shown in the drawings since they do not differ in any respect from conventional circuits employed in the prior art.

This structure is in accordance with the teachings of the European patent cited earlier except in regard to the formation of the overdoped electrolyte zone $E_{12}$ in accordance with the present invention.

A second cell has been constructed and is of the same type as the cell just described but does not have the above-mentioned zone $E_{12}$.

Figure 6:
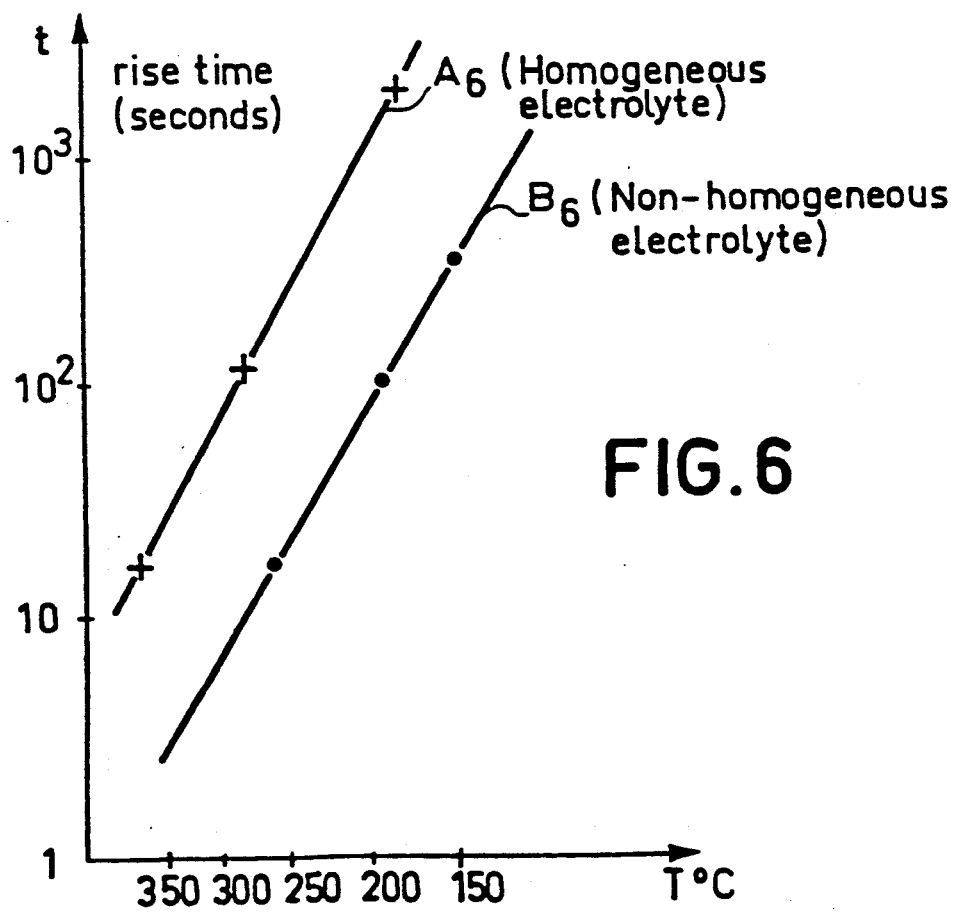
FIG. 6 is a diagram in which the response time of a sensor of the prior art is compared with the response time of a sensor fabricated in accordance with the teachings of the present invention.

The rise times of the interelectrode electromotive force of said cells in response to a one-step variation in partial pressure of oxygen have been compared. The results are grouped together in the diagram of FIG. 6 in the case of temperatures within the range of 150° to 350° C. whilst all other parameters remain identical.

The rise time is conventionally defined as being the time taken to change from 10 to 90% of the difference between the old and new value of the interelectrode electromotive force.

Curve $A_6$ relates to a homogeneous-electrolyte sensor and curve $B_6$ relates to an inhomogeneous-electrolyte sensor in accordance with the teachings of the invention. The rise times of the last-mentioned sensors are ten times shorter than those of a homogeneous-electrolyte sensor.

Apart from zirconia, other materials are suitable for the formation of the two electrolyte regions and different methods may also be employed to this end. Suitable materials are listed in the table which appears at the end of this description but are given solely by way of example and not in any limiting sense. The doping materials are elements of columns IIA and IIIB of the Periodic Table.

It is worthy of note that a specific doping percentage which is capable of optimizing the ionic conduction within region $E_{11}$ of the electrolyte corresponds to each pair consisting of principal material and dopant.

The invention is not limited to solid electrolytes which are ionic conductors for oxygen but also extends to all electrolytes which are ionic conductors for a halogen. One example of a halogen of this type is fluorine. In this case the principal material can be lead fluoride ($PbF_2$) or an association of lead fluoride and stannic fluoride ($PbF_2/SnF_2$) or else the materials having the chemical formulae : $SrF_2$, $BaF_2$, $SrBr_2$, $CaF_2$, $BaCl_2$. The doping material is an alkaline element.

In a second alternative embodiment of the invention, it is possible to increase the ion exchange currents at the interface between solid electrolyte and external medium, not by surface overdoping of the solid electrolyte but by depositing on this latter a thin film of a second material which has also been doped.

In fact, if consideration is again given to the case of detection of oxygen as described earlier, the work of escape of an atom of oxygen to the external medium (electrode $E_2$) is substantial. In consequence, only a small number of oxygen atoms of the zirconia lattice will be endowed with sufficient energy to escape from the lattice and take part in the exchange currents.

On the other hand, if consideration is given to yttrium-doped ceric oxide having the composition $(CeO_2)_{0.97} (Y_2O_3)_{0.03}$, the work of escape of an atom of oxygen is of much lower value, thus resulting in a higher value of current for exchange with the external medium.

In a second alternative embodiment of the invention, a second surface region $E_{12}$ of the electrolyte is formed by depositing a thin film on the first region $E_{11}$. The materials of these two regions are different and the work function of the material of the second region in respect of a species to be detected must be lower than that of the first region $E_{11}$.

Figure 7:
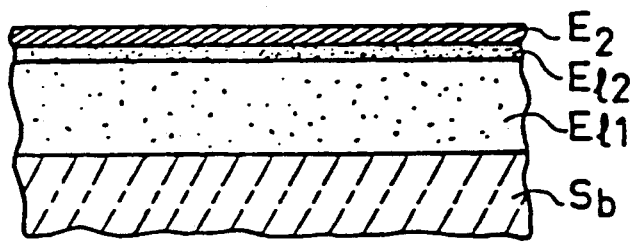
FIG. 7 shows one example of an electrochemical sensor fabricated in accordance with a second alternative embodiment of the invention.

FIG. 7 is a schematic illustration of a sensor constructed in accordance with the second alternative embodiment of the invention. The different elements already described are again shown: the substrate $S_b$ and the first region $E_{11}$ of the electrolyte. In accordance with the second alternative embodiment, the second region $E_{12}$ of the electrolyte is formed by a thin film of doped material which also forms a solid electrolyte. Finally, the measuring electrode $E_2$ is again shown but the reference electrode $E_1$ has been omitted from this figure.

In regard to deposition of the thin film which forms the second region $E_{12}$ of the electrolyte, the methods usually employed for fabrication of integrated circuits are suitable for this purpose. By way of example, the deposit can be obtained by vacuum evaporation or by cathodic sputtering.

Figure 3:
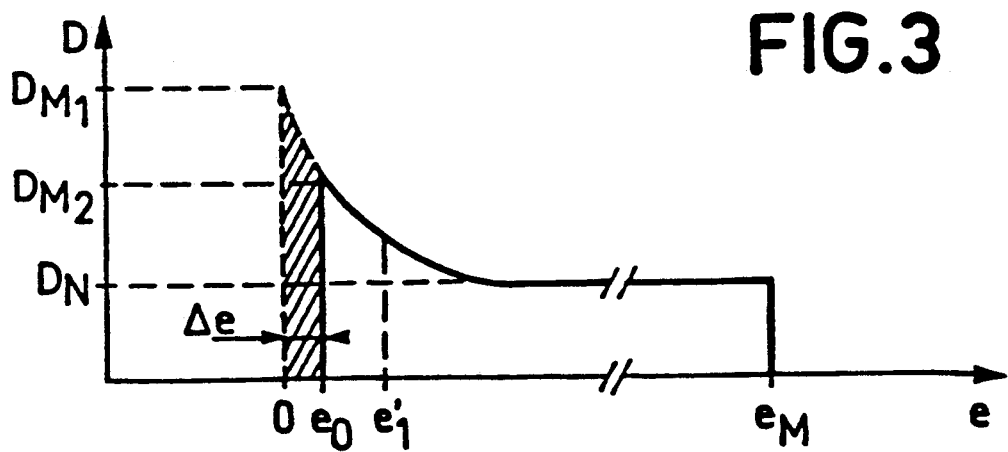

Should the method employed be too fast to obtain a sufficiently thin film, the method described with reference to FIG. 3 may again be adopted. Preferably, the thickness of the second region is smaller than 400 Å.

Deposition may take place only in certain zones of the surface of the principal electrolyte $E_{11}$. In this case, recourse is had to masking techniques which are well-known to those versed in the art.

The invention is not limited solely to the examples of construction which have been described in the foregoing by way of illustration.

It is possible in particular to form a third region by overdoping of the principal electrolyte $E_{11}$ or deposition of a thin film in the zone of contact between electrolyte and second electrode. This proves necessary in particular when this electrode is not of the "M-MX" type described earlier, that is, of the type in which the functions of electrode and reference medium are combined.

Finally, the invention is applicable to devices other than electrochemical sensors, such as solid-electrolyte devices for production or storage of electrical energy.

TABLE

| Solid electrolyte: Region $E_{11}$: | |
|---|---|
| principal material: | $ZrO_2$, $CeO_2$, $HfO_2$, $ThO_2$ |
| dopant: | $CaO$, $Yb_2O_3$, $Sc_2O_3$, $Y_2O_3$, $Gd_2O_3$, $Nd_2O_3$, $La_2O_3$ |
| method of fabrication: | sintering, evaporation, sputtering, implantation, ... |
| Surface layer, Region $E_{12}$: | |
| principal material: | $ZrO_2$, $CeO_2$, $HfO_2$, $ThO_2$ |
| dopant: | $CaO$, $Yb_2O_3$, $Sc_2O_3$, $Y_2O_3$, $Gd_2O_3$, $Nd_2O_3$, $La_2O_3$ |
| method of fabrication: | sintering, evaporation, sputtering, implantation |

What is claimed is:

1. An electrochemical cell comprising first and second electrodes in contact with a solid electrolyte comprised of a first region having a composition $M_{1-x}Z_x$ wherein M is selected from the group consisting of $ZrO_2$, $CeO_2$, $HfO_2$ and $ThO_2$, and Z is selected from the group consisting of $CaO$, $Yb_2O_3$, $Sc_2O_3$, $Gd_2O_3$, $Nd_2O_3$ and $La_2O_3$, wherein $0.07 \leq X \leq 0.20$ and a second surface region having a thickness less than 400 angstroms overlaying said first region at least at that portion of said first region subjacent to said first electrode, said second surface region having a composition $M_{1-y}Z_y$ wherein M and Z have the identities selected for said first region, wherein $Y > 0.15$ and wherein $Y > X$, such that said second region comprises an overdoped region of ionic conductivity lower than that of said first region.

2. The electrochemical cell of claim 1, wherein M is $ZrO_2$ and Z is $CaO$.